(12) United States Patent
Doerr

(10) Patent No.: US 9,101,277 B2
(45) Date of Patent: Aug. 11, 2015

(54) MEDICAL SENSOR SYSTEM

(75) Inventor: Thomas Doerr, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 561 days.

(21) Appl. No.: 13/494,974

(22) Filed: Jun. 12, 2012

(65) Prior Publication Data
US 2012/0330123 A1    Dec. 27, 2012

Related U.S. Application Data

(60) Provisional application No. 61/500,622, filed on Jun. 24, 2011.

(51) Int. Cl.
*A61B 5/04* (2006.01)
*A61N 1/05* (2006.01)
*A61B 5/042* (2006.01)
*A61M 39/02* (2006.01)

(52) U.S. Cl.
CPC .............. *A61B 5/042* (2013.01); *A61N 1/0502* (2013.01); *A61N 1/0504* (2013.01); *A61B 2562/0209* (2013.01); *A61B 2562/227* (2013.01); *A61M 39/0208* (2013.01); *A61M 2205/04* (2013.01); *A61M 2205/3303* (2013.01)

(58) Field of Classification Search
CPC .... A61B 5/0408; A61B 5/042; A61B 5/0422; A61B 5/0478; A61B 5/0492; A61B 5/6813; A61B 5/6837; A61B 5/6839; A61B 5/6848; A61B 5/685; A61B 5/6865; A61B 5/6868; A61B 2562/0209; A61B 2562/227; A61N 1/0502; A61N 1/0504; A61N 1/0531; A61N 1/0539; A61N 1/36003; A61N 1/36017

USPC ......... 600/372, 373, 375, 377, 378, 544–546, 600/548, 509; 607/115, 116, 48
See application file for complete search history.

(56) References Cited

U.S. PATENT DOCUMENTS

| | | | |
|---|---|---|---|
| 4,041,946 A * | 8/1977 | Barton ....................... 604/93.01 |
| 4,151,835 A * | 5/1979 | Showell et al. ............... 600/376 |
| 5,144,952 A * | 9/1992 | Frachet et al. ................ 600/379 |
| 6,144,867 A * | 11/2000 | Walker et al. ................. 600/340 |
| 6,643,552 B2 | 11/2003 | Edell et al. |
| 6,865,907 B2 * | 3/2005 | Andrews et al. .................. 63/12 |
| 7,917,222 B1 | 3/2011 | Osorio et al. |
| 8,744,582 B2 * | 6/2014 | Wahlstrand et al. ............ 607/36 |
| 2002/0109621 A1 * | 8/2002 | Khair et al. .................... 341/174 |

(Continued)

OTHER PUBLICATIONS

European Search Report, dated Oct. 15, 2012, 7 pages.

*Primary Examiner* — Lee S Cohen
*Assistant Examiner* — Erin M Cardinal
(74) *Attorney, Agent, or Firm* — ARC IP Law, PC; Joseph J. Mayo

(57) ABSTRACT

A medical sensor system which includes at least one sensor lead which can be implanted in the body of a human/animal, comprising two end sections, wherein the end sections are designed to be routed through two artificial openings in the surface of the body. The sensor lead includes, between the two end sections, at least one sensor for detecting a biological measured quantity. The sensor system furthermore includes at least one fastening element disposed on the surface of the body, which can be connected to the end sections guided through the body openings for affixing the implanted sensor lead, wherein the at least one fastening element comprises a device for processing sensor signals, and an energy source for supplying the sensor system with electrical energy.

16 Claims, 8 Drawing Sheets

(56) References Cited

U.S. PATENT DOCUMENTS

| | | | |
|---|---|---|---|
| 2003/0046954 A1* | 3/2003 | Ashton | 63/12 |
| 2003/0120328 A1* | 6/2003 | Jenkins et al. | 607/116 |
| 2005/0182455 A1 | 8/2005 | Thrope et al. | |
| 2009/0062893 A1* | 3/2009 | Spehr et al. | 607/116 |
| 2009/0085768 A1 | 4/2009 | Patel et al. | |
| 2009/0240188 A1* | 9/2009 | Hyde et al. | 604/20 |
| 2010/0152812 A1 | 6/2010 | Flaherty et al. | |
| 2012/0035451 A1* | 2/2012 | Jaffe et al. | 600/373 |

\* cited by examiner

MEDICAL SENSOR SYSTEM

This application claims the benefit of U.S. Provisional Patent Application 61/500,622 filed on 24 Jun. 2011, the specification of which is hereby incorporated herein by reference.

BACKGROUND OF THE INVENTION

1. Field of the Invention

At least one embodiment of the invention applies to the field of medical engineering and relate to a medical sensor system comprising a sensor lead which can be implanted in the body of a human or an animal and comprises one or more sensors for detecting biological measured quantities.

2. Description of the Related Art

The contraction of the heart is based on electrical stimulation that is generated in the sinoatrial node in the normal case, and is transmitted by the heart's natural conducting system to the cardiac muscle cells. The voltage changes that occur as a result can be measured on the surface of the body using electrodes, thereby enabling findings regarding the state and diseases of the heart to be obtained on the basis of the variation over time (ECG=electrocardiogram). For instance, the electrocardiogram can be used to detect cardiac arrhythmias, for instance, in particular tachycardias and bradycardias, and ventricular extrasystoles.

Cardiac arrhythmias often do not occur during an examination in a medical office or in the hospital, but rather in certain situations, such as during physical exertion or during the night. It is common practice to attach a wearable ECG recorder to patients for recording a so-called long-term ECG for a period of 24 hours or longer, for instance. Electrodes connected to the ECG recorder are adhered to the patient's chest and record the electrical signals. This is uncomfortable to the patient, since the adhered electrodes interfere with personal hygiene, and the ECG recorder is usually visible as it is carried on the body. In addition, the adhered electrodes can easily become detached, and so such a wearable ECG recorder is not suitable for use to perform an extended observation of the electrical signals of the heart, e.g. for a period of several weeks, months, or years.

ECG recorders that can be implanted in the patient's body are known in medical practice. In that particular case, an ECG recorder in the form of a fully encapsulated implant is implanted in the patient to be monitored, in an implant pocket subcutaneously or submuscularly close to the heart. The implant is typically equipped with a telemetry interface via which information can be requested. A disadvantage of implantable ECG recorders is the fact that implantation is relatively complex, and the implant pocket must be opened as soon as diagnostics have been completed or the implant battery is exhausted. This is difficult for the patient, leaves a relatively large scar, and is associated with a significant risk of infection due to the implant pocket. A further disadvantage involves the relatively large dimensions of the implant, which are determined mainly by the battery size, which depends on the service life, the size of the antenna for the telemetry interface, and the biocompatible encapsulation of the implant. Implants are therefore usually relatively large in practical application. As a result, the implants are not adapted with the primary aim of obtaining an optimal ECG reading, nor can they always be placed in the most favorable location with respect to the ECG reading, due to specific anatomical circumstances, thereby possibly resulting in poorer quality diagnostics. A further disadvantage is posed by the relatively high costs of such an implantable ECG recorder, since all components must meet the demands of an implantable medical device, the battery must be designed large enough to prevent the need to remove it prematurely, and a relatively expensive telemetry interface must be provided. Moreover, acceptance problems arise with young patients in particular, since such an implant wears out, and, as mentioned above, the implantation leaves a relatively large scar. In addition, the implant can present a contraindication for certain diagnostic and therapeutic procedures (e.g. a nuclear resonance tomographic examination).

BRIEF SUMMARY OF THE INVENTION

The problem addressed by at least one embodiment of the invention is therefore that of preventing the stated disadvantages of implantable or wearable ECG recorders known from the prior art. This and other problems are solved, according to at least one embodiment of the invention, by a medical sensor system having the features as claimed herein. Advantageous embodiments of at least one embodiment of the invention are also claimed herein.

According to at least one embodiment of the invention, a sensor system for a medical application is shown. The sensor system comprises at least one sensor lead that can be implanted in the body of a human or an animal and comprises at least one sensor for detecting a biological measured quantity. The expression "implantable" as used here refers to permanent installation in the body, e.g. for a period of a few weeks, a few months, or a few years. The expression also refers to a brief, temporary installation in the body of a patient, e.g. during an examination. The sensor lead of the medical sensor system is preferably designed for subcutaneous implantation.

According to at least one embodiment of the invention, the implantable sensor lead comprises two end sections which are designed to be inserted into the surface of the body through two artificial openings in the body, thereby enabling the two end sections to be contacted on the surface of the body. The at least one sensor is located in an intermediate section of the implanted sensor lead disposed between the two end sections. The sensor can be designed as a biophysical or biochemical sensor in particular. Furthermore, the sensor can be an active sensor that requires electrical energy to record a measured quantity and generate sensor signals, or it can be a passive sensor that can record a measured quantity and emit sensor signals without a supply of electrical energy.

The sensor system furthermore comprises at least one fastening element disposed on the surface of the body, which, to be fixed in position, can be connected or is connected to the end sections of the sensor lead which were routed through the openings in the body. For this purpose, the two end sections and the at least one fastening element are equipped with suitable connections, such as threaded, clamped, plug, detent, or clip connections.

In the sensor system according to at least one embodiment of the invention, the at least one fastening element comprises a device for processing or for example that is configured to process signals from the sensor, and an energy source for supplying the sensor system with electrical energy.

Diverse designs of the device for processing sensor signals are possible, and the expression "processing of sensor signals" can be broadly interpreted. For example, the device can be used in particular to store, process, evaluate, provide, and/or transmit the sensor signals. For this purpose, the device for processing sensor signals is electrically connected to the at least one sensor when the sensor lead is connected to the at least one fastening element. In particular, the sensor lead is designed to direct sensor signals emitted by the at least one sensor to at least one of the two end sections, in particular to both end sections, thereby enabling the sensor signals to be easily transmitted to the device for processing sensor signals when the sensor lead is connected to the at least one fastening element.

The energy source can be used to store energy for the device for processing sensor signals and/or for the sensor. For this purpose, the energy source is electrically connectable or connected to the device for processing sensor signals and/or to the sensor. The device for processing sensor signals typically comprises a microprocessor and is programmed in a suitable manner for processing the sensor signals.

The sensor system according to at least one embodiment of the invention therefore advantageously makes it possible to implant only the sensor lead comprising the at least one sensor in the body, subcutaneously in particular, wherein the device for processing sensor signals and the energy source for operating the system are located on the surface of the body, thereby enabling the sensor lead to be designed with small dimensions. As a result, the sensor lead can be implanted very easily and with a greatly reduced risk of complications, and, in particular, can be temporarily explanted. Implantation takes place through the two openings in the body for the end sections, the diameter of which is at least approximately the same as that of the sensor lead, thereby ensuring that no scars or only very small scars remain after the implant is removed. In addition, the sensor lead and the at least one fastening element disposed on the surface of the body can be designed to be very appropriate from an aesthetic perspective. The at least one fastening element makes it possible to affix the sensor lead in the patient's body in a reliable, secure manner. Since the at least one fastening element does not need to meet the special requirements of an implantable medical component, the sensor system can be created easily and at low cost.

In general, the at least one fastening element of the sensor system can have any design provided it is ensured that the implanted sensor lead is affixed and the device for processing sensor signals and the energy source are provided. In an advantageous embodiment of the sensor system according to at least one embodiment of the invention, the at least one fastening element is flexible in order to enable adaptation to the contour of the body surface, thereby resulting in particularly effective affixation of the sensor lead. In addition, the wearing comfort for the patient and the asthetic appearance of the sensor system can be improved, thereby improving the patient's acceptance of the sensor system.

The at least one fastening element is connectable or connected to the two end sections of the sensor lead that are routed through the openings in the body. It is advantageous for the at least fastening element to be detachably connectable to the two end sections of the sensor lead, thereby enabling it to be detached from the end sections and reattached thereto. The option to repeatedly fasten the at least one fastening element to the two end sections makes it possible, in a particularly advantageous manner, to replace and/or repair the at least one fastening element without the need to remove the implanted sensor lead. In particular, the energy source (battery) of the sensor system can be easily recharged and/or replaced, thereby making it possible in particular to use relatively inexpensive (e.g. smaller) energy sources. However, the at least one fastening element can also be removed in order to read out data from the device for processing sensor signals, thereby also making it possible to eliminate a relative expensive telemetry interface for transmitting sensor signals or data based thereon.

In the sensor system according to at least one embodiment of the invention, the implantable sensor lead can be rigid or flexible in design, wherein it can be advantageous in terms of recording measured quantities for the sensor lead to be flexible, e.g. so that the at least one sensor can be placed at a site that is particularly anatomically suitable for recording the signal. In addition, it is advantageous for the end sections of the sensor lead to be flexible and/or curved or bent, thereby enabling them to be easily routed through the two openings in the surface of the body.

In a further advantageous embodiment of the sensor system according to at least one embodiment of the invention, the sensor lead comprises a constant (unchanged) lead diameter and/or no abrupt changes in the lead diameter, thereby making it possible to remove and reimplant the sensor lead in a particularly simple manner. In particular, it could even by removed by the patient himself, if necessary.

As described, the sensor system according to at least one embodiment of the invention comprises at least one fastening element for affixing the implanted sensor lead in the patient's body. In an advantageous embodiment, a single fastening element, which is connectable or connected to the two end sections of the sensor lead is provided for affixing the implanted sensor lead. The single fastening element can be flexible in design, in particular, for adaptation to the contour of the body surface, in order to fasten the sensor lead in a reliable and secure manner. The single fastening element can be permanently connected to one of the two end sections, wherein it is movable relative to the sensor lead, and can be connected to the other end section of the sensor lead. For this purpose, the sensor system can include e.g. a carrier made of a flexible material, wherein the device for processing sensor signals and the energy source for supplying the sensor system with electrical energy are fastened to the carrier, and wherein the sensor lead has the shape of a reinforced structure of the carrier. In particular, the carrier can be designed to be suitable for the application of printed circuits to enable electrical connections between the various electrical components to be easily attained. This embodiment results in a particularly simple design of the sensor system, which enables the sensor lead to be implanted very rapidly. For this purpose, it is only necessary to bring the sensor lead—which has already been connected to the fastening element on an end section—into a position that is suitable for implantation, which is made possible by the flexible connection to the fastening element, and, once the sensor lead has been implanted, to connect the other end section of the sensor lead to the fastening element.

In an alternative embodiment of the sensor system according to at least one embodiment of the invention, two fastening elements are provided for affixing the sensor lead, each of which is connectable or connected to one of the two end sections of the sensor lead. This embodiment also makes it possible to reliably and securely affix the sensor lead that has been implanted in the body, even when rigid fastening elements are used, if necessary, which can be made smaller compared to the previous embodiment of the sensor system comprising a single fastening element. In particular, the sensor system can be designed such that a fastening element comprises the device for processing sensor signals, and the other fastening element comprises the energy source, thereby enabling the device for processing sensor signals and the energy source to be replaced and/or repaired independently of one another. For example, data can be read out of the device for processing sensor signals without simultaneously removing the energy supply to the system. Alternatively, the sensor system can also be designed such that only one of the two fastening elements comprises the device for processing sensor signals and the energy source, while the other fastening element merely performs a fastening or closing function.

As described above, the sensor signals can be read out e.g. when the at least one fastening element is removed from the sensor lead. It can also be advantageous for the device used to process sensor signals to include a telemetry unit having a telemetry interface for the wireless transmission of sensor signals and/or data based thereon to an electronic device outside of the body, or to be coupled thereto for purposes of data transmission.

In a further advantageous embodiment of the sensor system according to at least one embodiment of the invention, the sensor lead comprises at least one active agent depot for delivering one or more active agents to the body. In particular, active agents that prevent infection or promote epithelization can be introduced into the body in this manner.

In a further advantageous embodiment of the sensor system according to at least one embodiment of the invention, said sensor system comprises a securing device for detaching the connection between the at least one fastening element and the two end sections of the sensor lead. This measure prevents the connection from becoming detached accidentally and/or without authorization.

In a further advantageous embodiment of the sensor system according to at least one embodiment of the invention, the sensor lead is designed as a bipolar electrode lead comprising at least one electrode, wherein the electrode is used to detect electrical signals in the patient's body, in particular electrical voltages associated with heart contractions. The electrode can be designed, in particular, as an electrically conductive surface region for receiving electrical signals from the electrode lead, wherein the electrode can basically also be used to emit electrical pulses, i.e. to transmit electrical energy to the surroundings. "Pole" is another typical term for electrode. The at least one electrode of the electrode lead is connected to an electrical supply lead, via which it is electrically connectable or connected, at one or both end sections, to the device for processing sensor signals. The surface of the electrode lead is typically electrically insulated, with the exception of the at least one electrode. The sensor system can be designed as an ECG recorder in particular.

It is understood that the various embodiments of the sensor according to the invention can be realized individually or in any combination. In particular, the features mentioned above and to be described below can be used not only in the combinations described, but also in other combinations or alone, without leaving the scope of the invention.

BRIEF DESCRIPTION OF THE DRAWINGS

The invention is explained in greater detail with reference to embodiments, and reference is made to the attached drawings. Elements that are the same or similar-acting are labeled using the same reference numerals. In the drawings.

DETAILED DESCRIPTION OF THE INVENTION

Figure 8:
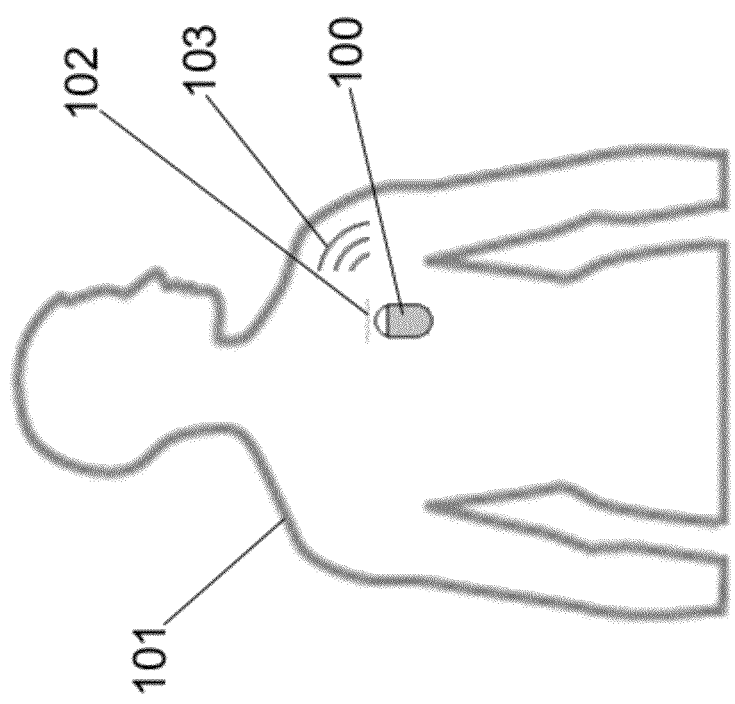
FIG. 8 shows a schematic depiction of a conventional ECG recorder implanted in a patient's body.

FIG. 8 will be considered first, which shows a fully encapsulated ECG recorder 100 according to the prior art, implanted in a patient's body. ECG recorder 100 is implanted close to the heart of a patient 101 in an implant pocket 102. ECG recorder 100 comprises a telemetry device, which is not depicted in greater detail, having a telemetry interface via which data 103 can be requested of the implant using close-field or far-field telemetry. The disadvantages of such an implant were addressed above.

Figure 1:
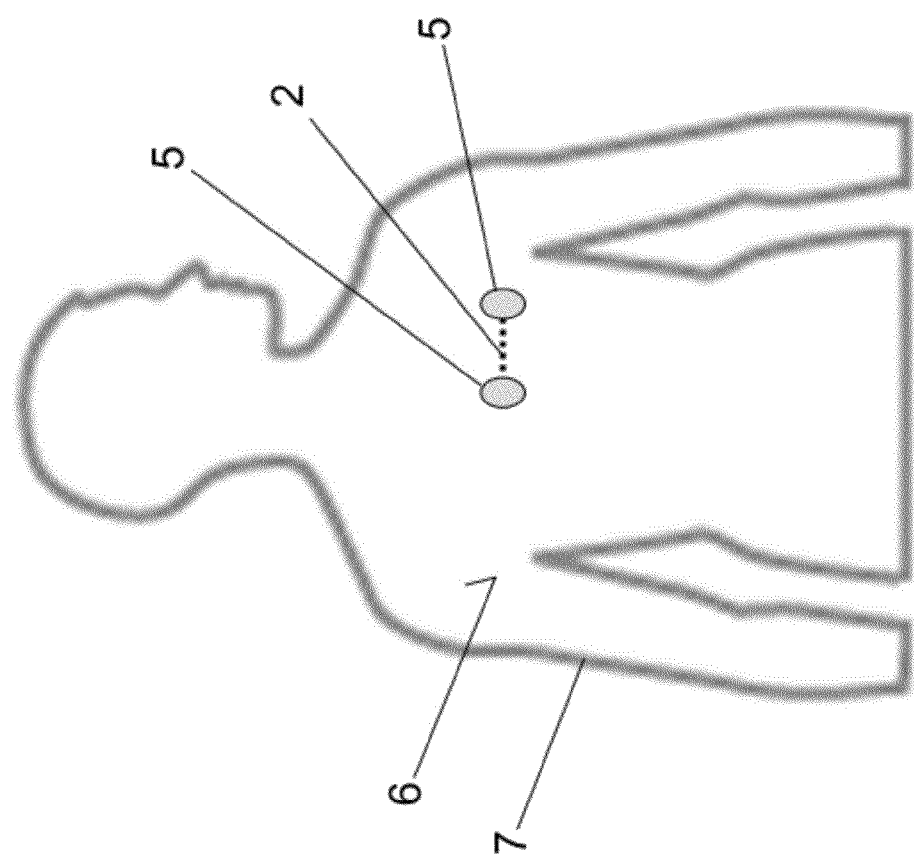
FIG. 1 shows a schematic depiction of a patient for illustration of an implanted sensor lead.
Figure 2:
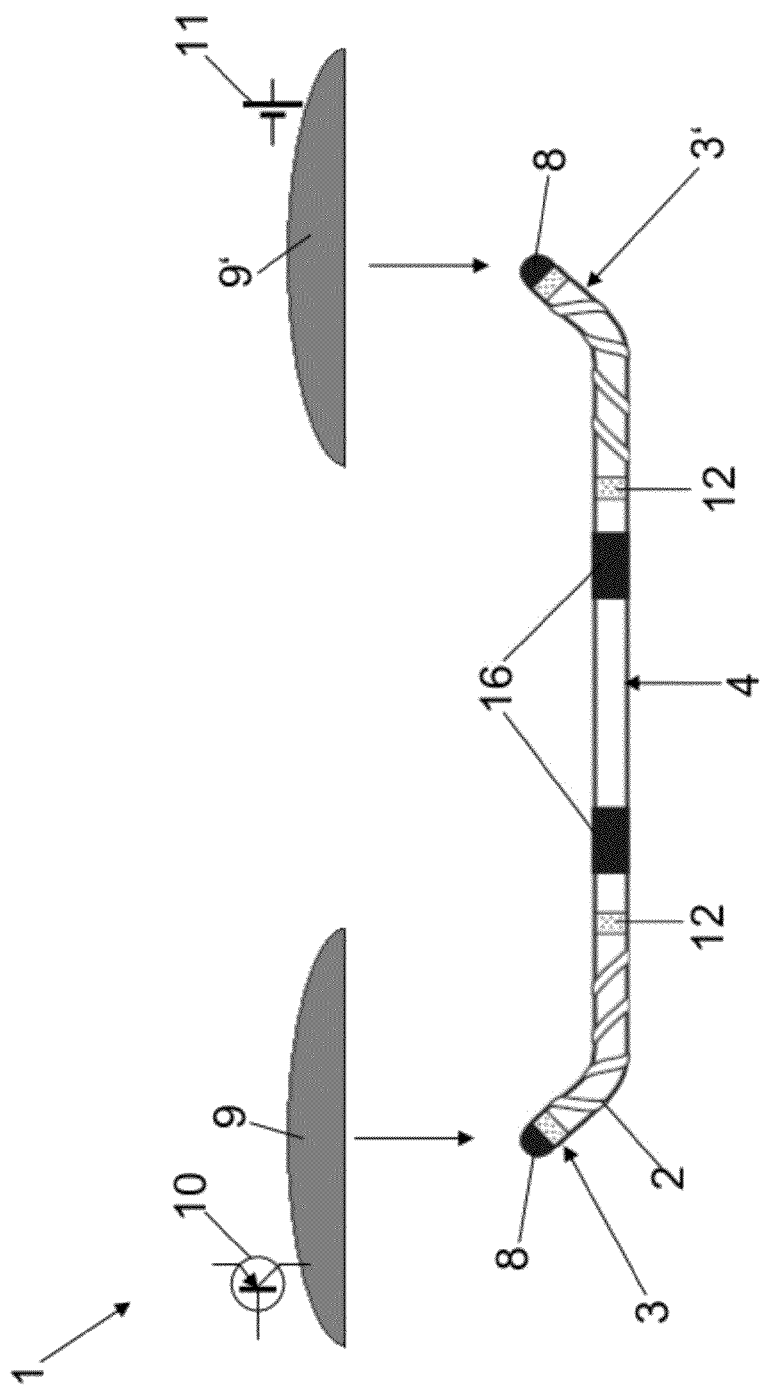
FIG. 2 shows a schematic depiction of an embodiment of the sensor system according to an embodiment of the invention.
Figure 3:
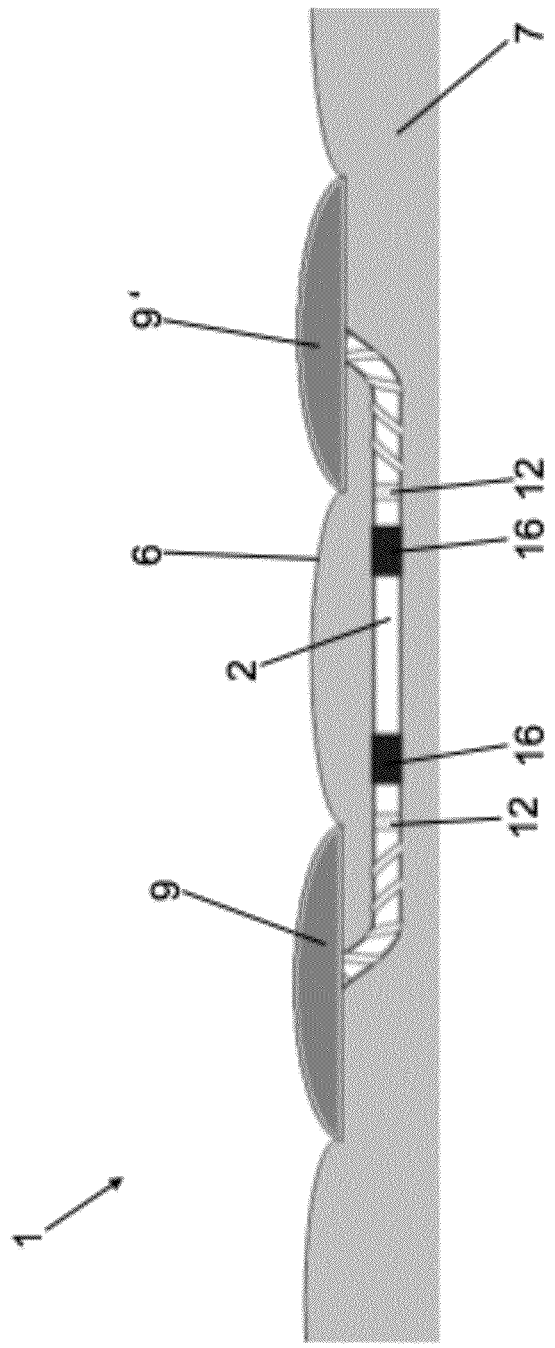
FIG. 3 shows a schematic depiction of the sensor system represented in FIG. 2, implanted in a patient's body.

FIGS. 1 to 3 show a first embodiment of the sensor system according to an embodiment of the invention, which is labeled in entirety using reference numeral 1. Sensor system 1 comprises a sensor lead for subcutaneous implantation, which is designed e.g. as a bipolar (ECG) electrode lead 2 in this case. Electrode lead 2 can be subdivided—in one or more embodiments, into two end sections 3, 3' and an intermediate section 4 located between the two end sections 3, 3'. The subdivision is attained in this case by the shape of electrode lead 2, for example, wherein the two straight end sections 3, 3' form an obtuse angle with straight intermediate section 4, but can also have a curved or bent shape.

As shown in FIG. 1, electrode lead 2 can be implanted subcutaneously close to the heart of a patient 7. In the case of implanted electrode lead 2, each of the two end sections 3, 3' is routed through an artificial body opening or perforation site 5, and so electrode lead 2 comes to rest at both ends thereof against body surface 6 of patient 7. Intermediate section 4 therefore has a subcutaneous position, while the two end sections 3, 3' each extend from a subcutaneous position to body surface 6. In terms of functionality, the two end sections 3, 3' can therefore differ from intermediate section 4 such that end sections 3—in contrast to intermediate section 4—are used to route sensor lead 2 through the two perforation sites 5 in body surface 6.

Electrode lead 2 can be flexible or rigid. In particular, the two end sections 3, 3' are flexible, and/or are curved or bent to enable adaptation to the shape of the body in the region of perforation sites 5. As shown in FIG. 2, electrode lead 2 has a symmetrical design with respect to a plane of symmetry that passes through the center of intermediate section 4.

In intermediate section 4, i.e. between the two end sections 3, 3', electrode lead 2 comprises two electrodes or electrical poles 16 which are used as sensors for electrical signals and are located on either side of the plane of symmetry. The two poles 16 are used in this case to record ECG signals. Although two poles 16 are shown, it is understood that a greater or fewer number of poles 16 can be provided. Poles 16 are each designed as electrically conductive surface region of electrode lead 2, while the remaining surface of electrode lead 2 is electrically insulated. The two poles 16 are electrically contacted via an electrical supply lead (not shown), wherein the ECG signals are transmitted by the supply lead to the two end sections 3, 3'.

A connection or contact device 8 is installed on each of the two end sections 3, 3' of electrode lead, by way of which the two end caps 9, 9' on implantable electrode lead 2 can be fastened in a removable (reusable) manner. In this case, the two end caps 9, 9' comprise a rigid housing having a flat or planar underside, which comes to rest on body surface 6. End caps 9, 9', due to the relatively small size thereof, lie on resilient body surface 6 at least approximately with an exact fit, as illustrated in FIG. 3. Implanted electrode lead 2 is fixed in position in the body of patient 7 by way of the two end caps 9, 9'. The two connection and contact devices 8 for connecting end caps 9, 9' can be designed e.g. as easily detached and reusable threaded, clamped, plug, detent, or clip connections. Advantageously, connection and contact devices 8 are designed such that a special tool is required to detach them, and therefore the connections can only be detached by an authorized person, in particular medical personnel. In this manner it is also possible to prevent patient 7 from detaching the connection in this embodiment.

The two end caps 9, 9' have functions in addition to fixing electrode lead 2 in position. For example, a microprocessor-based diagnostic unit 10 for processing ECG signals is integrated into one end cap 9, as indicated in FIG. 3 using a transistor symbol. Diagnostic unit 10 is electrically connected via the stated supply lead to both poles 16 as soon as end cap 9 is connected to associated end section 3 of electrode lead 2, thereby enabling the ECG signals to be redirected to diagnostic unit 10. The ECG signals can be stored and processed in diagnostic unit 10, and can be analyzed in particular, wherein data that reflect analytical results can be generated on the basis of the ECG signals. For instance, diagnostic unit 10 comprises, in particular, an electronic data memory (not shown) for storing ECG signals or data based thereon, which can be designed as a replaceable memory card (e.g. SD chip card), for example.

An energy source in the form of a battery 11—which is indicated in FIG. 3 using a symbol for a positive pole/negative pole—is integrated into the other end cap 9'. Battery 11 supplies electrical energy to diagnostic unit 10 for processing ECG signals, wherein battery 11 is electrically connected to device 10 via electrode lead 2 for this purpose. Likewise, an active sensor could be supplied with electrical energy by battery 11.

In sensor system 1, battery 11 and diagnostic unit 10 can be removed from electrode lead 2 independently of one another. Battery 11 can therefore be easily recharged or replaced, thereby making it possible for battery 11 to be designed relatively small in size, e.g. in the form of button cells which are low-cost and generally available. Likewise, diagnostic unit 10 can be easily repaired or replaced, wherein it is made possible in particular for the data memory—which is used to store ECG signals or data based thereon—to be read out by an external reading device at period intervals, for example. Likewise, removing end cap 9 from electrode lead 2 provides access to a replaceable memory card, in order to remove the memory card and read out data stored thereon. The same memory card or another memory card can then be inserted into end cap 9. Basically, it would also be feasible for end cap 9 to be designed such that a replaceable memory card can be removed even without removing end cap 9 of electrode lead 2 from end cap 9.

Optionally, end cap 9 can also comprise a telemetry unit, which has an integrated telemetry interface (not shown) and is coupled to diagnostic unit 10, for the wireless transmission of recorded ECG signals or data based thereon. The telemetry unit can be designed, in particular, to transmit the data to a wearable patient device that then forward said data to a service center for evaluation by medical personnel (e.g. a physician). In this manner, it is possible in particular to monitor the patient in real time (bio watch).

As shown in FIGS. 2 and 3, electrode lead 2 also comprises a plurality of active agent depots 12 for the elution of active agents which can have the effect, for instance, of inhibiting infection or promoting epithelization. Active agent depots 12 are located in intermediate section 4 on either side of the two electrical poles 16, although they can also be located in the two end sections 3, 3'. A person skilled in the art is very familiar with the design and function of such active agent depots 12, and so they will not be discussed further here.

To apply sensor system 1, the first step is to implant electrode lead 2 subcutaneously, wherein it is introduced into the body through a puncture channel and is affixed at the two exit or perforation sites 5 on the skin of patient 7 using the two end caps 9, 9'. Once the wound has healed, it can be assumed that the puncture channel has been fully epithelized along electrode lead 2, thereby rendering infection unlikely. This applies in particular when the epithelization-promoting active agents are released from active agent depots 12. In this case, electrode lead 2 is isodiametric in design, for instance, i.e. it has a constant diameter and has no abrupt changes in diameter. This makes it possible to remove electrode lead 2 temporarily after the wound has healed (approximately 4 to 8 weeks), and to then reinsert it into the existing skin channel. This can be performed by medical personnel or even patient 7, since this procedure does not create a new injury to body surface 6.

Sensor system 1 is therefore an ECG recorder, in the case of which only electrode lead 2 is implanted subcutaneously.

Figure 4:
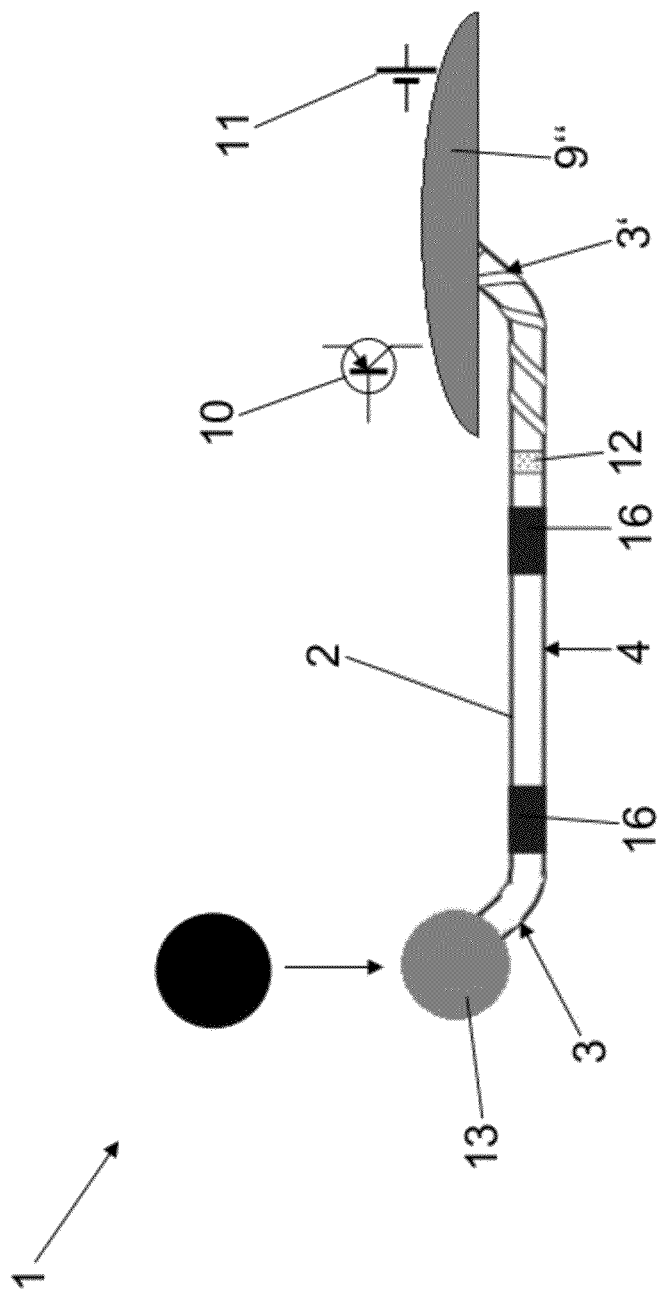
FIG. 4 shows a schematic depiction of a further embodiment of the sensor system according to an embodiment of the invention.

A further embodiment of sensor system 1 is shown in FIG. 4. To avoid unnecessary repetition, only the differences from sensor system 1 shown in conjunction with FIGS. 1 to 3 will be explained, and reference is made to the explanations therein for the rest. Accordingly, sensor system 1 comprises an electrode lead 2 which is permanently connected to an end cap 9" at an end section 3'. Diagnostic unit 10 (which is coupled to a telemetry unit, if necessary) and battery 11 are integrated in end cap 9". At other end section 3, electrode lead 2 can be connected to an end piece 13, which is spherical in this case, for instance, by a threaded connection, for instance. End piece 13 is used only to affix electrode lead 2 implanted in the body of patient 7 in position. For application, electrode lead 2 connected to end cap 9" is implanted through a perforation point 5, where only end piece 13 must be fastened to be affixed in position on free end section 3 of electrode lead 2.

Figure 5:
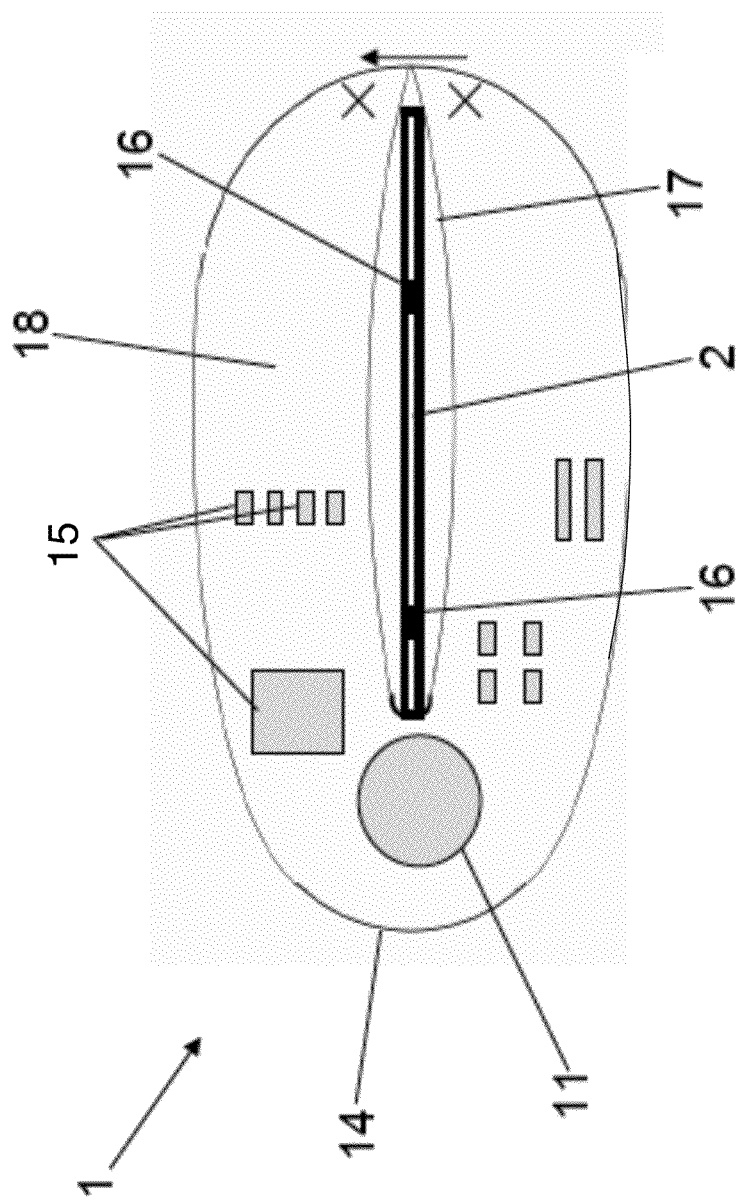
FIG. 5 shows a schematic depiction of a further embodiment of the sensor system according to an embodiment of the invention.
Figure 6A:
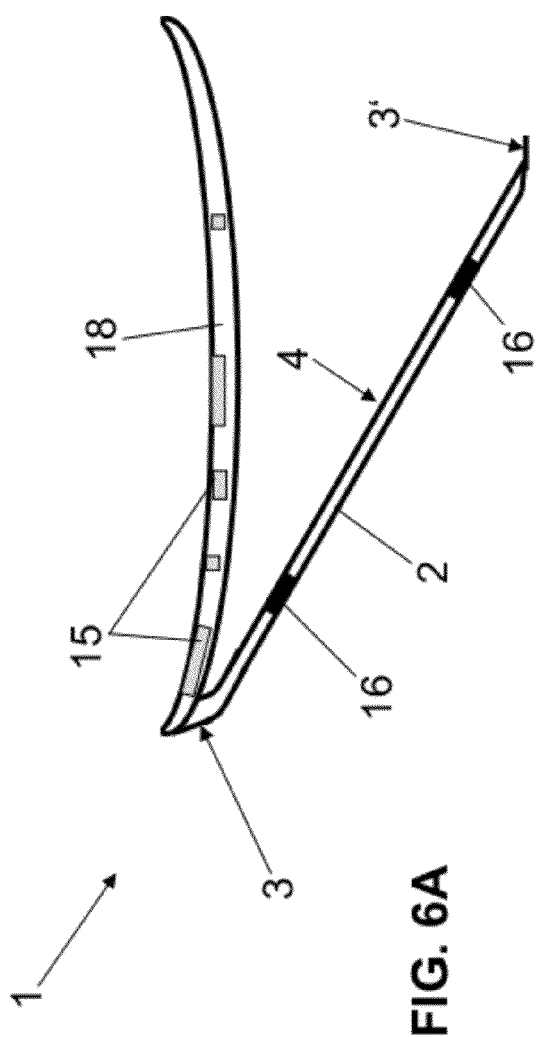
FIG. 6A-6B show further schematic depictions of the sensor system represented in FIG. 5.
Figure 6B:
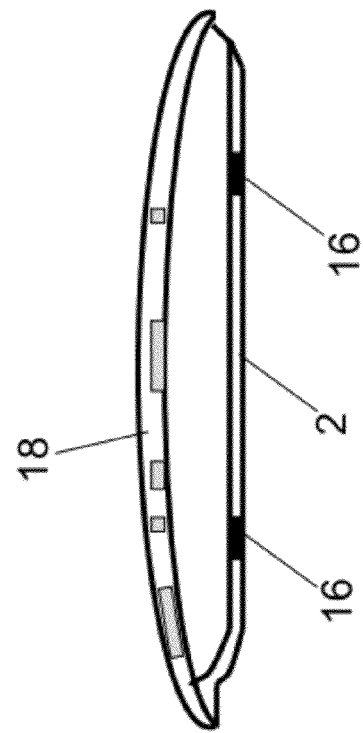
Figure 7:
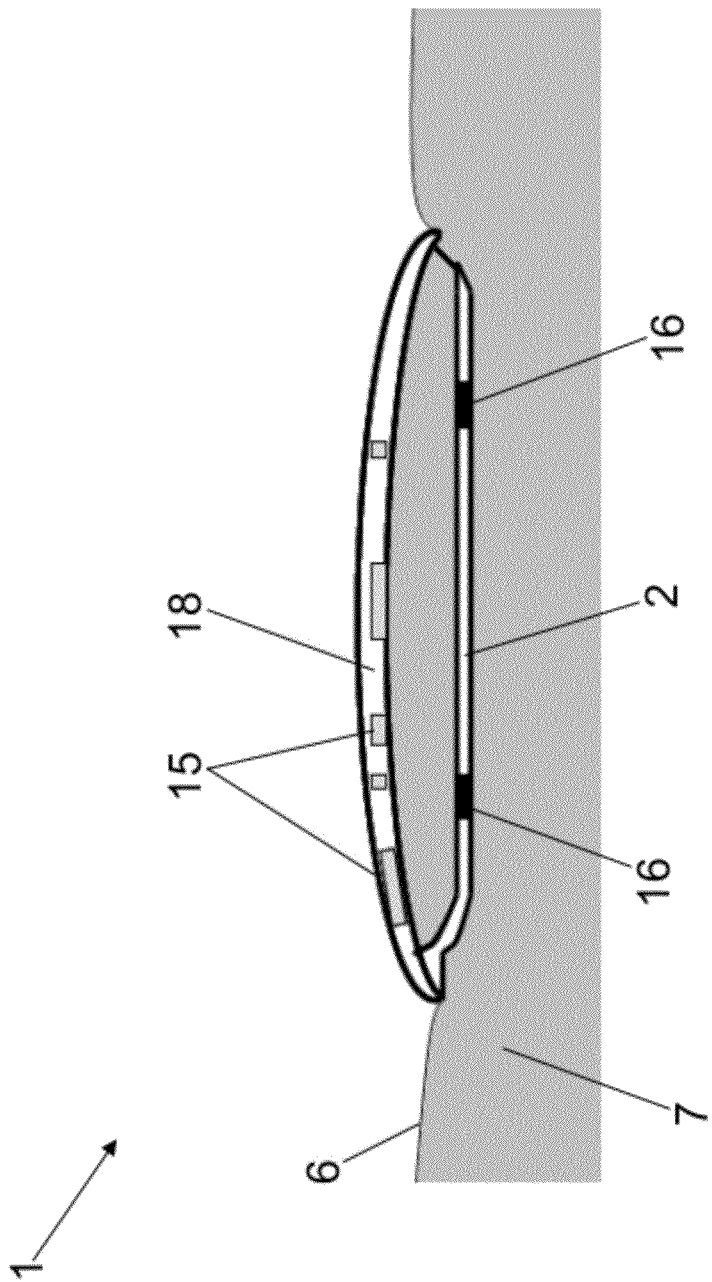
FIG. 7 shows a schematic depiction of the sensor system represented in FIG. 5, implanted in a patient's body.

A further embodiment of sensor system 1 is shown in FIGS. 5 to 7. To avoid unnecessary repetition, only the differences from the embodiment shown in FIGS. 1 to 3 will be explained, and reference is made to the explanations therein for the rest. Accordingly, sensor system 1 comprises a substrate or carrier 14 composed of a flexible material having an at least approximately oval contour, for instance, in this case. Carrier 14 is preferably composed of a biocompatible material, in particular a polymer material, such as a liquid crystal polymer (LCP). Electronic components 15 of diagnostic unit 10 and battery 11 are fastened on carrier 14 or are integrated therein. Preferably, carrier 14 is composed of a material that is suitable for printed circuits, thereby enabling the wiring for battery 11 and electronic components 15 to be easily printed on carrier 14. For protection against environmental influences, the various electronic or electrical components can be covered by a cover layer or cap (not shown). Furthermore, a reinforced structure is formed out of carrier 14 as a needle-shaped electrode lead 2. Electrode lead 2—except for an end section at which it is connected to remaining carrier section 18—is located in the region of a free punch 17. Electrode lead 2 is provided with two electrically conductive poles 16 for recording ECG signals.

Carrier 14 can be placed one over the other and interconnected, e.g. riveted, at the points labelled with "X" in FIG. 5, and therefore sensor system 1 has a clip-type structure in which electrode lead 2 can be moved relative to remaining carrier section 18 due to the flexibility of the carrier material. FIG. 6A shows a first, opened state with electrode lead 2 spread apart, and FIG. 6B shows a second, closed state with electrode lead 2 folded back together. In the opened state, needle-shaped electrode lead 2 can be introduced into a subcutaneous channel; in the closed state, implanted electrode lead 2 is fixed in position. As shown in FIG. 7, only needle-shaped electrode lead 2 is located under the skin, and remaining carrier section 18 lies on the surface of the skin for affixation of electrode lead 2.

As explained in detail with reference to the embodiments, at least one embodiment of the invention makes it possible to permanently implant a sensor lead comprising one or more sensors in the body of a patient ("diagnostic piercing"), wherein implantation can be carried out very easily and with a greatly reduced risk of complication. The sensor lead can be removed very easily and, in particular, temporarily. In particular, low-cost and replaceable components for energy supply can be used in the sensor system, thereby enabling the size of the implanted part of the sensor system to be greatly reduced. The sensor lead can be designed to be cosmetically appealing, and no scars or only very small scars are left after explantation. In addition, a telemetry function can be omitted and, instead, a (standard) storage medium for data can be used, in particular a memory card, which can be read out by an external reading device.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE CHARACTERS

1 Sensor system
2 Electrode lead
3, 3' End section
4 Intermediate section
5 Performation point
6 Body surface
7 Patient
8 Connection device
9, 9', 9" End cap
10 Diagnostic unit
11 Battery
12 Active agent depot
13 End piece
14 Carrier
15 Electronic component
16 Pole
17 Free punch
18 Carrier section
100 ECG recorder
101 Patient
102 Implant pocket
103 Data

What is claimed is:

1. A medical sensor system, which comprises:
    at least one sensor lead configured to be implanted in or near a body surface of a body of a human or an animal, comprising
        two end sections configured to be routed through two artificial body openings in the body surface, wherein said two end sections comprises a first end section and a second end section opposite to said first end section;
        an intermediate section disposed between the two end sections; and
        at least one sensor located in said intermediate section and configured to detect a biological measured quantity between the two end sections and emit sensor signals therefrom; and,
    two fastening elements configured to be disposed on the body surface and connected to the two end sections routed through the two artificial openings in the body surface to affix the at least one sensor lead, wherein the two fastening elements comprise
        a first fastening element connected to the first end section of the two end sections,
            wherein said first fastening element comprises a device configured to process sensor signals, and
        a second fastening element connected to the second end section of the two end sections, wherein said second fastening element comprises an energy source configured to supply electrical energy;
    wherein the at least one sensor lead directs said sensor signals to at least said first end section, such that said sensor signals are transmitted to said device configured to process sensor signals.

2. The sensor system according to claim 1, wherein at least one fastening element of the two fastening elements is flexible in order to enable adaptation to the contour of the body surface.

3. The sensor system according to claim 1, wherein at least one fastening element of the two fastening elements is detachably connectable to a respective end section of the at least one sensor lead.

4. The sensor system according to claim 1, wherein the at least one sensor lead is flexible.

5. The sensor system according to claim 1, wherein the at least one sensor lead has a constant lead diameter and/or does not have any abrupt changes in diameter.

6. The sensor system according to claim 1, wherein the first fastening element connected to the first end section is movable relative to the at least one sensor lead.

7. The sensor system according to claim 1, wherein the device configured to process signals from the at least one sensor is coupled to a telemetry device having a telemetry interface configured to transmit sensor signals and/or data based thereon.

8. The sensor system according to claim 1, wherein the at least one sensor lead comprises at least one active agent depot configured to release one or more active agents into the body.

9. The sensor system according to claim 1, further comprising a securing device configured to prevent detachment of a connection between at least one fastening element of the two fastening elements and a respective end section of the at least one sensor lead.

10. The sensor system according to claim 1, wherein the at least one sensor lead is configured as a bipolar electrode lead, the at least one sensor comparing at least one electrode configured to detect electrical signals.

11. The sensor system according to claim 1, wherein the at least one sensor comprises an active sensor supplied with electrical energy to detect said biological measured quantity and generate sensor signals.

12. The sensor system according to claim 1, wherein said energy source stores energy for said device configured to process sensor signals, said at least one sensor, or both said device configured to process sensor signals and said at least one sensor.

13. The sensor system according to claim 1, wherein at least one fastening element of the two fastening elements is detachably connectable such that said at least one fastening element is attached and reattached to a respective end section to replace and/or repair the at least one fastening element.

14. The sensor system according to claim 1, wherein said first fastening element is detachably connectable and configured to be removed to read out said sensor signals or data from said device for processing sensor signals.

15. The sensor system according to claim 1, wherein the at least one sensor comprises a passive sensor that records a measured quantity and emits said sensors signals without a supply of electrical energy.

16. A medical sensor system, which comprises:
  at least one sensor lead configured to be implanted in or near a body surface of a body of a human or an animal, comprising
    two end sections configured to be routed through two artificial body openings in the body surface;
    an intermediate section disposed between the two end sections; and
    at least one sensor located in said intermediate section and configured to detect a biological measured quantity between the two end sections and emit sensor signals therefrom; and,
  at least one fastening element configured to be disposed on the body surface and connected to the two end sections routed through the two artificial openings in the body surface to affix the at least one sensor lead, wherein the at least one fastening element comprises
    a device configured to process sensor signals, and
    an energy source configured to supply electrical energy;
  wherein the at least one sensor lead directs said sensor signals to at least one of the two end sections, such that said sensor signals are transmitted to said device configured to process sensor signals, and,
  wherein the at least one sensor lead is flexible.

* * * * *